(12) United States Patent
Sakano et al.

(10) Patent No.: US 7,781,604 B2
(45) Date of Patent: Aug. 24, 2010

(54) FLUORINE-CONTAINING ACRYLATE

(75) Inventors: Yasunori Sakano, Annaka (JP);
Noriyuki Koike, Takasaki (JP);
Hirofumi Kishita, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 12/619,135

(22) Filed: Nov. 16, 2009

(65) Prior Publication Data

US 2010/0147191 A1   Jun. 17, 2010

(30) Foreign Application Priority Data

Dec. 11, 2008   (JP)   ............................. 2008-316050

(51) Int. Cl.
*C07C 7/10* (2006.01)
(52) U.S. Cl. ........................ 556/406; 556/419; 556/420
(58) Field of Classification Search ................ 556/406, 556/419, 420
See application file for complete search history.

(56) References Cited

U.S. PATENT DOCUMENTS

2007/0116971 A1   5/2007   Yoshikawa et al.

FOREIGN PATENT DOCUMENTS

| EP | 0 320 537 | 6/1989 |
|---|---|---|
| EP | 2 151 444 | 2/2010 |
| JP | 5-194322 A | 8/1993 |
| JP | 07-118279 | 5/1995 |
| JP | 11-349651 A | 12/1999 |

OTHER PUBLICATIONS

Kobunshi Ronbun-shu "Surface properties and the surface molecular chain aggregation structure of fluoroalkyl acrylate polymer thin film", vol. 64, No. 4, pp. 181-190, Apr. 2007.
European Search Report issued Mar. 8, 2010, in European Application No. 09178350.6.

*Primary Examiner*—Elvis O Price
(74) *Attorney, Agent, or Firm*—Birch, Stewart, Kolasch & Birch, LLP

(57) ABSTRACT

The present invention is a fluorine-containing acrylate or alpha-substituted, fluorine-containing acrylate, represented by the following formula (1):

$$\left[\begin{array}{c} Rf \\ | \\ (Z)_c \\ | \\ (CH_2)_2 \\ | \\ Si-O \\ | \\ CH_3 \end{array}\right]_a \left[\begin{array}{c} O-R^1-\underset{\underset{O}{\|}}{C}-\underset{\underset{H}{|}}{N}-R^2 \\ | \\ (CH_2)_3 \\ | \\ Si-O \\ | \\ CH_3 \end{array}\right]_b \quad (1)$$

wherein a is an integer of from 1 to 4 and b is an integer of from 1 to 4, provided that a total of a and b is 3, 4, or 5;
$R^1$ is a group represented by the following formula (2):

$$-(C_4H_8O)_d(C_3H_6O)_e(C_2H_4O)_f(CH_2O)_g- \quad (2)$$

wherein d, e, f, and g are, independently of each other, an integer of from 0 to 4, provided that a molecular weight of $R^1$ is in a range of 30 to 300, and these repeating units may be sequenced at random;
$R^2$ is an acryl group- or alpha-substituted acryl group-containing group having 4 to 20 carbon atoms and represented by the following formula (3):

$$R^4 \!\!\left(\!\!-\!O\!-\!\underset{\underset{O}{\|}}{C}\!-\!\underset{\underset{R^3}{|}}{C}\!=\!CH_2\right)_{\!n} \quad (3)$$

wherein $R^3$ is, independently of each other, a hydrogen atom, a fluorine atom, a methyl group, or a trifluoromethyl group,
$R^4$ is a divalent or trivalent linking moiety having 1 to 18 carbon atoms, optionally having an ether bond and/or an ester bond, and
n is 1 or 2;
Rf is a perfluoropolyether residue represented by the following formula (4):

$$-CF\!\!\left(\!O\!-\!CF_2\!-\!\underset{\underset{CF_3}{|}}{CF}\!\right)_{\!j}\!\!\left(O\!-\!CF_2\!-\!CF_2\!-\!CF_2\right)_{\!k}\!- \quad (4)$$
$$\underset{X}{|} \qquad -(O-CF_2-CF_2)_l(O-CF_2)_m-F$$

wherein j, k, l, and m are, independently of each other, an integer of from 0 to 50, provided that a molecular weight of Rf is in a range of 200 to 6000,
X is a fluorine atom or a trifluoromethyl group, and these repeating units may be sequenced at random;
Z is a divalent organic group; and
c is 0 or 1.

7 Claims, No Drawings

FLUORINE-CONTAINING ACRYLATE

CROSS REFERENCES

This application claims the benefits of Japanese Patent Application No. 2008-316050 filed on Dec. 11, 2008, the contents of which are hereby incorporated by reference.

FIELD OF THE INVENTION

The present invention relates to a photo-curable fluorine-containing acrylate, particularly to a fluorine-containing acrylate or alpha-substituted, fluorine-containing acrylate which has a cyclosiloxane structure and good compatibility with non-fluorine solvents. Both of the fluorine-containing acrylate and the alpha-substituted, fluorine-containing acrylate are hereinafter collectively referred to as "a fluorine-containing acrylate".

BACKGROUND OF THE INVENTION

Conventionally, polymers obtained from polymerizable monomers which have a perfluoroalkyl group in a side chain, such as fluorine-containing alkyl ester of acrylic acid and a fluorine-containing alkyl ester of methacrylic acid, are widely known as a fluorine compound which can be cured by radiation of light, such as ultraviolet ray. As a typical example, an acrylate which has the following structure has widely been used in order to provide a substrate surface with water- and oil-repellency, stain resistance, abrasion resistance, and scratch resistance.

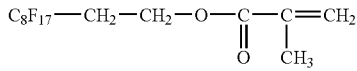

However, recently, there is an increasing tendency with environmental concerns to regulate use of compounds which have a long-chain perfluoroalkyl group having eight or more carbon atoms. Meanwhile, it is known that acrylic compounds having a perfluoroalkyl group with less than eight carbon atoms give worse surface property than ones having a perfluoroalkyl group with eight or more carbon atoms do (the following Non-Patent Literature 1).

Meanwhile, photo-curable fluorine compounds are known which have a perfluoropolyether group composed of an oxygen atom participating in an ether bond and a perfluoroalkyl group having three or less carbon atoms. For instance, Patent Literature 1 discloses the following acrylic compound which is derived from a hexafluoropropylene oxide oligomer.

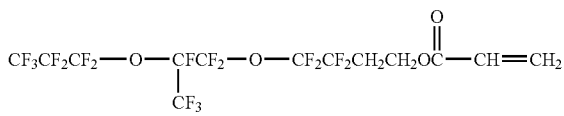

Patent Literature 2 discloses a urethane acrylate which is a reaction product of a fluorine-containing polyether diol with 2-isocyanatoethyl methacrylate. The urethane acrylate has bad compatibility with photo polymerization initiators, non-fluorinated acrylates, and non-fluorinated organic solvents due to the water- and oil-repellency of the fluorine-containing compounds and, therefore, can be blended with restricted number of components and has restricted usage.

[Non-Patent Literature 1]: Koubunshi Ronbun-Shu Vol. 64, No. 4, pp 181-190 (April, 2007).
[Patent Literature 1]: Japanese Patent Application Laid-Open No. Hei-5-194322
[Patent Literature 2]: Japanese Patent Application Laid-Open No. Hei-11-349651

DISCLOSURE OF THE INVENTION

Problems to be Solved by the Invention

The present inventors made researches for the purpose of providing a photo curable fluorine compound which has good compatibility with non-fluorine organic compounds, maintaining good properties as a fluorine compound (Japanese Patent Application Nos. 2008-195417 and 2008-315203). The present invention has been made as a part of the researches and provides a fluorine-containing acrylate having a specific oxyalkylene group which offers a better compatibility with non-fluorine organic compounds.

Means to Solve the Problems

Namely, the present invention is the following fluorine-containing acrylate or alpha-substituted, fluorine-containing acrylate represented by the following formula (1),

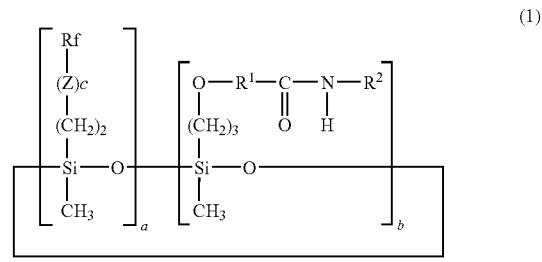

wherein a is an integer of from 1 to 4 and b is an integer of from 1 to 4, provided that a total of a and b is 3, 4, or 5;
$R^1$ is a group represented by the following formula (2),

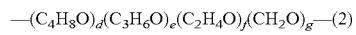

wherein d, e, f, and g are, independently of each other, an integer of from 0 to 4, provided that a molecular weight of $R^1$ is in a range of 30 to 300, and these repeating units may be sequenced at random;
$R^2$ is an acryl group- or alpha-substituted acryl group-containing group, having 4 to 20 carbon atoms and represented by the following formula (3),

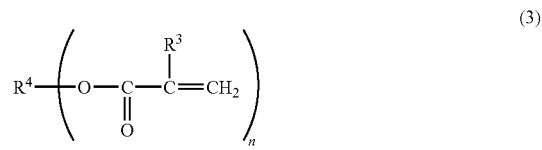

wherein $R^3$ is, independently of each other, a hydrogen atom, a fluorine atom, a methyl group, or a trifluoromethyl group;
$R^4$ is a divalent or trivalent linking moiety having 1 to 18 carbon atoms, optionally having an ether and/or ester bond, and
n is 1 or 2;

Rf is a perfluoropolyether residue represented by the following formula (4),

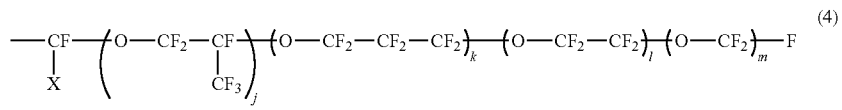

wherein j, k, l, and m are, independently of each other, an integer of from 0 to 50, provided that a molecular weight of Rf is in a range of 200 to 6000, X is a fluorine atom or a trifluoromethyl group, and these repeating units may be sequenced at random;

Z is a divalent organic group; and c is 0 or 1.

Effects of the Invention

The present fluorine-containing acrylate is good in compatibility with non-fluorinated organic compounds and, further, can be cured by light to form a cured product which is water- and oil-repellent. Accordingly, the present acrylate is useful as an additive for a non-fluorine hard coat as well as for a fluorine one.

BEST MODES TO WORK THE INVENTION

The present fluorine-containing acrylate is represented by the following formula (1).

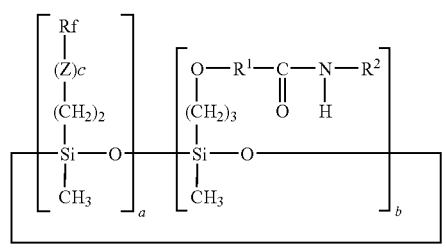

In formula (1), a is an integer of from 1 to 4, b is an integer of from 1 to 4, provided that a total of a and b is 3, 4, or 5. Preferably, a is 1 and b is 3 or 4. As will be described below, the afore-mentioned acrylate is prepared by reacting a hydrogen atom bonded to Si with an unsaturated group in a compound which is to form a side chain and, therefore, the constitution of the side chain can be changed by selecting a ratio of the compounds used. For instance, an acrylate with a=b=2 as well as an acrylate with a=1 and b=3 can be prepared. It is also possible to prepare a mixture of these, for instance, a mixture which contains 50 mole % of an acrylate with a=b=2 and 50 mole % of an acrylate with a=1 and b ~1, so that a=b=1.5 as a whole.

$R^1$ is a group represented by the following formula (2), $$—(C_4H_8O)_d(C_3H_6O)_e(C_2H_4O)_f(CH_2O)_g— \qquad (2)$$

wherein d, e, f, and g are, independently of each other, an integer of from 0 to 4, provided that a molecular weight of $R^1$ is in a range of 30 to 300, preferably 30 to 90. The repeating units may be sequenced at random.

As a particularly preferred example of the structures, mention may be made of the following threes, —$(C_2H_4O)_f$—
—$(C_3H_6O)_e$—
—$(C_4H_8O)_d$— wherein d, e and f each are 1 or 2 and a propylene group and a butylene group may be branched.

$R^2$ is an organic group having 1 to 20 carbon atoms which has at least one acryl group or alpha-substituted acryl group and is represented by the following general formula (3),

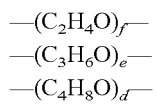

wherein $R^3$ is, independently of each other, a hydrogen atom, a fluorine atom, a methyl group, or a trifluoromethyl group, preferably a hydrogen atom or a methyl group;

$R^4$ is a divalent or trivalent linking moiety having 1 to 18 carbon atoms, optionally comprising an oxygen atom which forms an ether bond, an ester structure, and an acryl or methacryl structure, preferably a group included in the following formulas for $R^2$, particularly an ethylene group.

As the particularly preferred examples of $R^2$, the following can be mentioned.

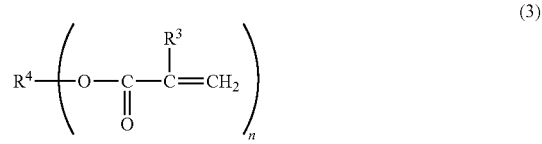

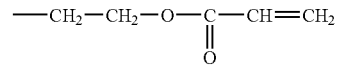

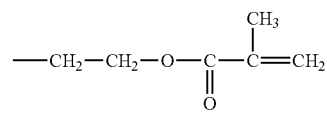

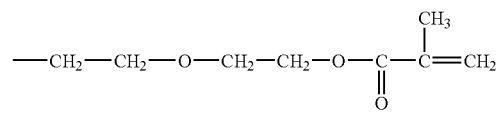

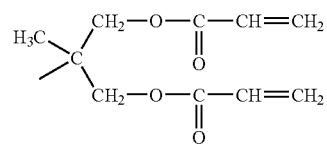

Rf is a perfluoropolyether residue represented by the following general formula (4), (4)

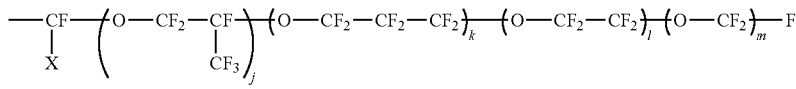

wherein j, k, l, and m are, independently of each other, an integer of from 0 to 50, preferably 2 to 15, provided that a molecular weight of Rf is in a range of 200 to 6000, preferably 400 to 2000. These repeating units may be sequenced at random. X is a fluorine atom or a trifluoromethyl group. As the particularly preferred Rf, the following groups can be mentioned.

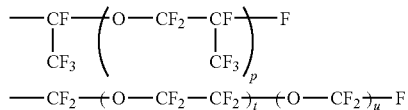

wherein p, t, and u each are an integer of from 1 to 30, preferably 2 to 15, particularly 3 to 10. Moieties, —OCF$_2$CF$_2$— and —OCF$_2$CF$_2$—, can be sequenced at random.

In formula (1), Z is a divalent organic group. The structure of Z is not particularly limited as far as Z can link Rf to an ethylene group and does not inhibit the polymerization of the acryl group. For instance, mention may be made of the following groups.

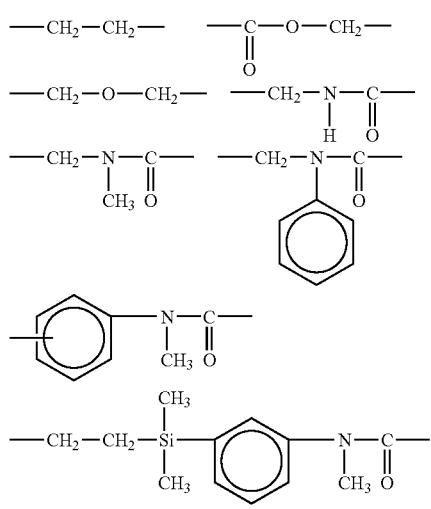

Among these, the following groups are particularly preferred.

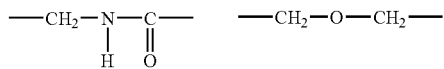

The present fluorine-containing acrylate can be prepared in the following process.

First, cyclic hydrogensiloxane (5) as represented by the following formula:

(5)

wherein s is 3, 4, or 5;

the following fluorine-containing olefin (6):

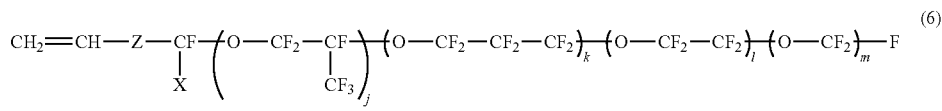

(6)

wherein X, j, k, l and m are as defined above; and alkyl alcohol having an allyl group at one end (7), $$CH_2=CH-CH_2-O-(C_4H_8O)_d(C_3H_6O)_e(C_2H_4O)_f(CH_2O)_g-H \qquad (7)$$

wherein d, e, f, g and h are as defined above, are subjected to addition reaction in the presence of a known catalyst comprising a metal of the platinum group to obtain a compound represented by the following formula (8).

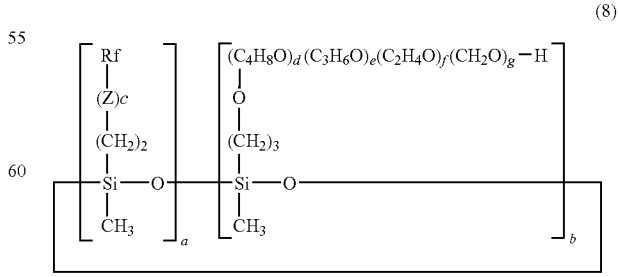

(8)

An OH group in the afore-mentioned (8) is reacted with the following compound (9):

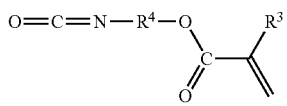

(9)

to obtain the compound having the structure of the afore-mentioned formula (1).

In the addition reaction of compounds (5), (6), and (7), the order of the reaction is not limited to any particular one. Preferably, (5) and (6) are addition reacted and, then, an excess amount of (7) relative to unreacted Si—H group is reacted, in order to avoid condensation between the hydroxyl group in (7) and the Si—H group in (5). Alternatively, (6) is first addition reacted with a largely excess amount of compound (5); unreacted (5) is removed for purification or an addition ratio of (6) to (5) is adjusted as desired by a separation means such as column chromatography; and, then, the addition reaction of (7) is carried out, so that the average addition ratio of each component can be controlled stricter.

The reaction between compounds (8) and (9) may proceed by blending the both compounds under mild conditions between 0 and 70 degrees C. The reaction rate may be accelerated by adding 0.001 to 2% by weight, preferably 0.001 to 0.5% by weight, of a suitable catalyst system, relative to the total reactants weight. Examples of the suitable catalyst system include tin derivatives such as tin acetate, dibutyltin dilaurate, dibutyltin dioctate, dibutyltin diacetate, dioctyltin dilaurate, dioctyltin dioctate, dioctyltin diacetate, and stannous dioctanoate; iron derivatives such as iron acetylacetonate; titanium alcolates such as titanium tetraisopropylate; and tertiary amines such as triethylamine and N-methylmorpholine. If desired, the reaction may be carried out under dilution with various kinds of solvents.

A preferable hard coat composition comprises a urethane acrylate as a major component. Examples of the urethane acrylates include a reaction product of a polyisocyanate with a (meth)acrylate having a hydroxyl group; a reaction product of a polyisocyanate, a polyester having terminal diols, and a (meth)acrylate having a hydroxyl group; and a reaction product of a polyol, an excess amount of diisocyanate, and a (meth)acrylate having a hydroxyl group. Inter alia, the present compound is preferably blended in a composition comprising a urethane acrylate which is a reaction product of a (meth)acrylate having a hydroxyl group selected from 2-hydroxyethyl(meth)acrylate, 2-hydroxy-3-acryloyloxypropylmethacrylate, and pentaerythritol triacrylate with a polyisocyanate selected from hexamethylene diisocyanate, isophorone diisocyanate, trilene diisocyanate, and diphenylmethane diisocyanate.

Examples of the other hard coat compositions which are suitable for the present compounds to be mixed in include one whose major component comprises from di- to hexa-functional (meth)acrylic compounds such as 1,6-hexanediol di(meth)acrylate, neopentyl glycol di(meth)acrylate, ethylene glycol di(meth)acrylate, ethylene oxide isocyanurate-modified di(meth)acrylate, EO-isocyanurate modified tri(meth)acrylate, trimethylolpropane tri(meth)acrylate, pentaerythritol tri(meth)acrylate, glycerol tri(meth)acrylate, tris(meth)acryloyloxyethyl phosphate, (2,2,2-tri-(meth)acryloyloxymethyl)ethyl hydrogen phthalate, glycerol tri(meth)acrylate, pentaerythritol tetra(meth)acrylate, ditrimethylolpropane tetra(meth)acrylate, dipentaerythritol penta(meth) acrylate, dipentaerythritol hexa(meth)acrylate, and sorbitol hexa(meth)acrylate; epoxyacrylates obtained by addition reaction of the afore-mentioned (meth)acrylic compounds with ethylene oxide, propylene oxide, epichlorohydrin, or an aliphatic acid-, alkyl-, or urethane-modified epoxy resin; and acrylate ester copolymers which have a (meth)acryloyl group in their side chain.

Various hard coat materials which can be cured with active energy ray, such as ultraviolet ray or electron beam, are commercially available from various companies. For instance, mention may be made of various trade names, such as "Beam Set" ex Arakawa Chemical Industries Ltd.; "Ubiq" ex Oohashi Chemical Industries Ltd.; "UV coat" ex Origin Electric Co., Ltd.; "Cashew UV" ex Cashew Co., Ltd.; "DeSolite" ex JSR Corporation; "Seika Beam" ex Dainichiseika Chemical Industries Co., Ltd.; "Shikoh" ex The Nippon Synthetic Chemical Industry Co., Ltd.; "Fujihard" ex Fujikura Kasei Co., Ltd.; "Diabeam" ex Mitsubisi Rayon Co., Ltd.; and "Ultra Vin" ex Musashi Paint Co., Ltd. The present compound can also be blended in a fluorinated type of a hard coat composition to increase, for instance, water repellency and oil repellency.

The present compound is blended in a hard coat composition and hardened to provide the coating with stain resistance, water repellency, oil repellency, and fingerprint proof property or to enhance such properties. The coating is resistant against fat of human being such as fingerprint, sebum and sweat, and cosmetics. Even when stain attaches to the coating, the stain is easily wiped off. Accordingly, the present compound can be used as an additive for curable compositions which are to be coated on a surface of articles, which surface may be touched by a human body and stained with human fat or cosmetics, to form a coating film or protective film thereon. Examples of the articles include optical recording media such as optical discs and hologram records, for instance, optical magnetic discs, CD's, LD's, DVD's, and blue ray discs; optical parts and optical devices such as lenses of glasses, prisms, lens sheet, pellicle films, polarizing plates, optical filters, lenticular lenses, Fresnel lenses, antireflection films, optical fibers, and optical couplers; screens or displaying devices such as CRT's, liquid crystal displays, plasma displays, electroluminescence displays, rear projection displays, fluorescent display tubes (VFD's), field emission projection displays and toner displays, particularly, image-displaying devices such as personal computers, mobile phones, personal digital assistants, game machines, digital cameras, digital camcorders, automated teller machines, cash dispensers, automatic vending machines, navigation devices of, for instance, automobiles, and security system terminals, and devices for displaying and inputting an image of touchpanel type with which the operation thereof is also carried out, such as touch sensors and touchscreens; inputting devices such as mobile phones, personal digital assistants, mobile music players, and handheld game machines, remote controllers, controllers, key boards and panel switches for in-car-devices; surfaces of housing of mobile phones, personal digital assistants, cameras, mobile music players, and handheld game machines; coatings and surfaces of exteriors of automobiles, pianos, classy furniture, and marble stones; parts made of transparent glass or plastic (acryls or polycarbonates) and various mirror members such as protective glass for exhibiting works of art, show windows, show cases, covers for advertisement, covers for photo stands, wrist watches, windshields for automobiles, window glass for trains and air planes, headlights and tail lamps of automobiles. The amount to be added is properly adjusted in a range of from 0.1 part by weight to 10 parts by weight relative to 100 parts by weight of a solid content of a hard coat composition, depending on desired oil repellency, solubility of the composition and curing conditions.

EXAMPLES

The present invention will be specifically explained by the following Examples but shall not be limited thereto.

Example

In a 100 ml three-necked flask equipped with a reflux device and a stirrer were placed 30.0 g of the fluorine-containing cyclosiloxane represented by the following formula (10),

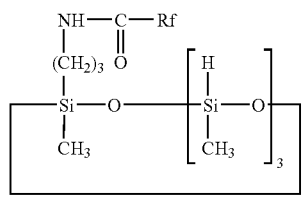

(10)

wherein Rf is the following group,

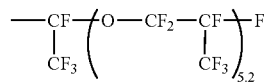

wherein the number of the repeating units has distribution with an average of 5.2, and 20.0 g of toluene under a dry nitrogen atmosphere and heated with stirring up to 90 degrees C. Then, a mixture solution of 10.3 g of ethylene glycol monoallyl ether with 0.010 g of a solution of vinylsiloxane-modified chloroplatinic acid in toluene (platinum content: $2.49 \times 10^{-8}$ mole) was added dropwise over 30 minutes and stirred at 90 degrees C. for 12 hours. The progress of the reaction was confirmed by the decrease in the peak height of Si—H group of compound (10) appearing at 4.8 ppm in $^1$H-NMR. The reaction solution was treated at 100 degrees C. and 1 Torr for 2 hours to remove unreacted ethylene glycol monoallyl ether.

To 32 g of the compound obtained, 8.20 g of 2-isocyanatoethyl acrylate and 0.01 g of dioctyltin laurate were added under a dry air atmosphere and stirred at 25 degrees C. for 12 hours to obtain the compound having the following average composition. The chemical shifts in the $^1$H-NMR and $^{19}$F-NMR spectra of the compound are as shown below.

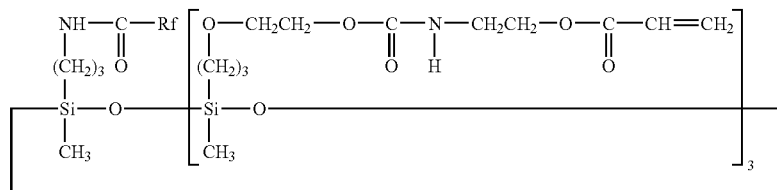

wherein Rf is as defined above.

Chemical shifts in $^1$H-NMR spectrum (Measuring device: JMN-LA300W ex JEOL, solvent: CDCl$_3$)

| Shift (TMS Reference) | |
|---|---|
| 0~0.3 ppm | —Si—C$\underline{H}_3$  12H |
| 0.4~0.6 ppm | —Si—C$\underline{H}_2$—C$\underline{H}_2$—  8H |
| 1.5~1.7 ppm | —Si—C$\underline{H}_2$—CH$_2$—CH$_2$—O—  6H |
|  | —Si—CH$_2$—C$\underline{H}_2$—CH$_2$—NH—  2H |
| 3.3~3.7 ppm | —Si—CH$_2$—C$\underline{H}_2$—CH$_2$—NH—  2H |
|  | —Si—CH$_2$—CH$_2$—C$\underline{H}_2$—O—CH$_2$—CH$_2$—O—  6H |
|  | —NH—CH$_2$—C$\underline{H}_2$—O—  6H |
|  | —Si—C$\underline{H}_2$—CH$_2$—CH$_2$—O—CH$_2$—CH$_2$—O—  6H |
| 4.0~4.5 ppm | —Si—CH$_2$—CH$_2$—CH$_2$—O—C$\underline{H}_2$—CH$_2$—O—CONH—CH$_2$—C$\underline{H}_2$—O—CO—  12H |
| 4.7~5.5 ppm | —Si—CH$_2$—CH$_2$—CH$_2$—O—CON$\underline{H}$—  3H |
| 5.8~6.5 ppm | —C$\underline{H}$=C$\underline{H}_2$  9H |
| 6.8~7.4 ppm | —Si—CH$_2$—CH$_2$—CH$_2$—N$\underline{H}$—  1H |

Chemical shifts in $^{19}$F-NMR

| Shift (F-11 Reference) | |
|---|---|
| −145.6 ppm | CF$_3$CF$_2$CF$_2$—O—C$\underline{F}$(CF$_3$)CF$_2$—O—CF(CF$_3$)—CO—NH—  1F |
| −132.7 ppm | —C$\underline{F}$(CF$_3$)—CO—NH—  1F |
| −130 ppm | CF$_3$C$\underline{F}_2$CF$_2$—O—  2F |
| −86~−79 ppm | C$\underline{F}_3$C$\underline{F}_2$C$\underline{F}_2$—O—CF(C$\underline{F}_3$)CF$_2$—O—CF(C$\underline{F}_3$)—CO—NH—  13F |

Comparative Example

In a 200 ml three-necked flask equipped with a reflux device and a mechanical stirrer were placed 15.5 g of 2-isocyanatoethyl methacrylate and 0.005 g of dioctyltin laurate under a dry air atmosphere. Then, 100 g of perfluoropolyether diol (ex Solvay Solexis, trade name: FOMBLIN D 2000, average molecular weight: 2000) was added dropwise at 50 degrees C. over 1 hour. After the completion of the addition, the reaction mixture was stirred at 50 degrees C. for 5 hours. In the IR spectra of the reaction product, the peak at 2300 $cm^{-1}$ which is attributed to —N=C=O group disappeared. The perfluoropolyether diol which has methacryl groups at both ends was obtained.

Each 0.5 g of the compounds of the Example and the Comparative Example was blended with 10 g of one of the different solvents described below to visually observe the solubility of each compound. The results are shown in Table 1, where + means that a transparent solution was obtained and − means that a transparent solution was not obtained.

TABLE 1

| Solvent | Example | Comparative Example |
| --- | --- | --- |
| Methanol | + | − |
| Ethanol | + | − |
| THF | + | − |
| Ethyl acetate | + | − |
| Acetone | + | − |
| PGMEA | + | − |
| DMSO | + | − |
| HFCF-225* | + | + |

*Asahiklin AK-225, ex Asahi Glass Co., Ltd.

As seen in Table 1, the compounds of the Example dissolve in more kinds of non-fluorinated solvents than conventional fluorine-containing acrylates do.

Evaluation on the Hard Coat Compositions 1

The compound prepared in the Example was blended in the following composition to prepare a solution. As a blank, a solution which did not contain any additive was also prepared.

| | |
| --- | --- |
| Ultra Vin Clear UV720KF ex Musashi Paint Co., Ltd. | 100 parts by mass |
| Ultra Vin Thinner Z 27095 ex Musashi Paint Co., Ltd. | 100 parts by mass |
| Additive (Compound of the Example) | 3 parts by mass |

Each solution was spin coated on a glass plate. It was irradiated with ultraviolet ray of 1.6 $J/cm^2$ in an ultraviolet irradiation device of a conveyer type to form a cured film. Each film was visually observed to evaluate its appearance. Water contact angles and oleic acid contact angles were measured on a contact angle meter ex Kyowa Interface Science Co., Ltd. The compound of the Comparative Example was too much less soluble to form a solution, so that it was impossible to prepare a hard coat.

Table 2 shows the properties of the surfaces which were treated with each hard coat. Felt pen repellency was evaluated by drawing a line on the surface with an oil-based marking pen ex Zebra Co., Ltd., High Macky, and visually observing how much its ink was repelled. A fingerprint wiping-off property was evaluated by pressing a forefinger on the surface to leave behind a fingerprint thereon, wiping the surface with tissue paper, and visually observing the wiping-off property.

TABLE 2

| | Additive | |
| --- | --- | --- |
| | None | Compound of the Example |
| Appearance | Transparent and colorless | Transparent and colorless |
| Water contact angle in degrees | 91 | 106 |
| Oleic acid contact angle in degrees | 44 | 75 |
| Felt pen repellency | Not repelled | Repelled |
| Fingerprint wiping-off property | Difficult to wipe off | Easy to wipe off |

Evaluation on the Hard Coat Compositions 2

The compound prepared in the Example was mixed in the following composition to prepare a solution. As a blank, a solution which did not contain any additive was also prepared.

| | |
| --- | --- |
| Tetra-functional acrylate (EBECRY 40, ex Daicel Cytec Co., Ltd.) | 100 Parts by mass |
| 1-Hydroxycyclohexyl phenyl ketone (Irgacure 184, ex Ciba in Japan) | 3 Parts by mass |
| Additive (compound of the Example) | 3 Parts by mass |

Each solution was spin coated on a glass plate. It was irradiated under a nitrogen atmosphere with ultraviolet ray of 1.6 $J/cm^2$ in an ultraviolet irradiation device of a conveyer type to form a cured film. Each film was visually observed to evaluate its appearance. Water contact angles and oleic acid contact angles were measured on a contact angle meter ex Kyowa Interface Science Co., Ltd. The compound of the Comparative Example was too much less soluble to form a solution.

Table 3 shows the results of the evaluation of the surfaces which were treated with each hard coat, made in the same way as in Evaluation 1.

TABLE 3

| | Additive | |
| --- | --- | --- |
| | None | Compound of the Example |
| Appearance | Transparent and colorless | Transparent and colorless |
| Water contact angle in degrees | 63 | 107 |
| Oleic acid contact angle in degrees | 24 | 75 |
| Felt pen repellency | Not repelled | Repelled |
| Fingerprint wiping-off property | Difficult to wipe off | Easy to wipe off |

As shown above, the present compound has good compatibility with non-fluorinated organic compounds and, therefore, can be used as an additive in compositions for surface hard coats of, for instance, glass, resins, films, paper, metals, ceramics, and wood; in compositions for surface protecting films of printed materials; and in painting composition.

The invention claimed is:

1. A fluorine-containing acrylate or alpha-substituted, fluorine-containing acrylate, represented by the following formula (1):

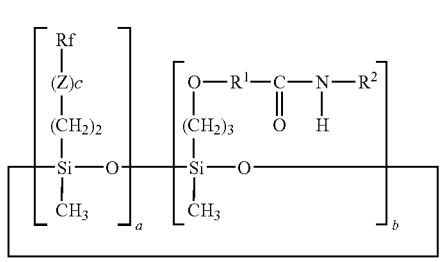

wherein a is an integer of from 1 to 4 and b is an integer of from 1 to 4, provided that a total of a and b is 3, 4, or 5;
$R^1$ is a group represented by the following formula (2):

 (2)

wherein d, e, f, and g are, independently of each other, an integer of from 0 to 4, provided that a molecular weight of $R^1$ is in a range of 30 to 300, and these repeating units may be sequenced at random;
$R^2$ is an acryl group- or alpha-substituted acryl group-containing group having 4 to 20 carbon atoms and represented by the following formula (3):

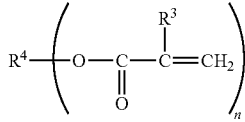 (3)

wherein $R^3$ is, independently of each other, a hydrogen atom, a fluorine atom, a methyl group, or a trifluoromethyl group,
$R^4$ is a divalent or trivalent linking moiety having 1 to 18 carbon atoms, optionally having an ether bond and/or an ester bond, and
n is 1 or 2;
Rf is a perfluoropolyether residue represented by the following formula (4):

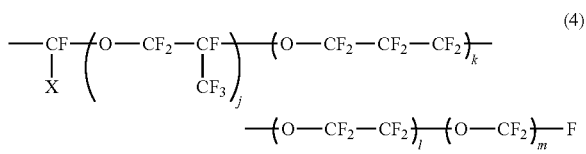 (4)

wherein j, k, l, and m are, independently of each other, an integer of from 0 to 50, provided that a molecular weight of Rf is in a range of 200 to 6000,
X is a fluorine atom or a trifluoromethyl group, and these repeating units may be sequenced at random;
Z is a divalent organic group; and
c is 0 or 1.

2. The fluorine-containing acrylate or alpha-substituted, fluorine-containing acrylate according to claim 1, wherein $R^1$ in formula (1) is a group represented by any of the following formulas:

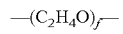

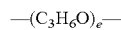

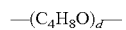

wherein d, e, and f each are 1 or 2.

3. The fluorine-containing acrylate or alpha-substituted, fluorine-containing acrylate according to claim 1 or 2, wherein $R^2$ in formula (1) is represented by any of the following formulas:

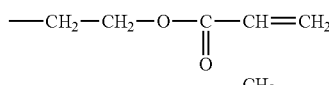

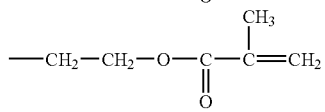

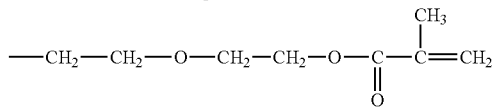

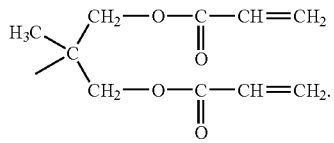

4. The fluorine-containing acrylate or alpha-substituted, fluorine-containing acrylate according to claim 1, wherein Rf in formula (1) is a group represented by the following formula,

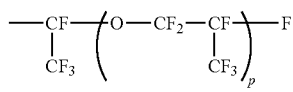

wherein p is an integer of from 1 to 30.

5. The fluorine-containing acrylate or alpha-substituted, fluorine-containing acrylate according to claim 1, wherein c in formula (1) is 1 and Z is a group represented by the following formula:

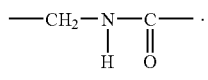

6. A hard coat composition comprising the fluorine-containing acrylate or alpha-substituted, fluorine-containing acrylate according to claim 1.

7. The hard coat composition according to claim 6, comprising a urethane acrylate as a major agent.

* * * * *